US008449827B2

United States Patent
Gelin

(10) Patent No.: US 8,449,827 B2
(45) Date of Patent: May 28, 2013

(54) REACTION WELL FOR AN AUTOMATIC ANALYSIS APPLIANCE

(75) Inventor: Jean-François Gelin, Creteil (FR)

(73) Assignee: Diagnostica Stago, Asnieres (FR)

( * ) Notice: Subject to any disclaimer, the term of this patent is extended or adjusted under 35 U.S.C. 154(b) by 614 days.

(21) Appl. No.: 12/523,823

(22) PCT Filed: Jan. 23, 2008

(86) PCT No.: PCT/FR2008/000082
§ 371 (c)(1),
(2), (4) Date: Jan. 14, 2010

(87) PCT Pub. No.: WO2008/110674
PCT Pub. Date: Sep. 18, 2008

(65) Prior Publication Data
US 2010/0143195 A1    Jun. 10, 2010

(30) Foreign Application Priority Data

Jan. 23, 2007  (FR) ...................... 07 00445

(51) Int. Cl.
*G01N 30/96* (2006.01)
*A61J 1/06* (2006.01)
*B01L 3/00* (2006.01)
*G01N 21/00* (2006.01)

(52) U.S. Cl.
USPC ............................................. 422/88; 422/554

(58) Field of Classification Search
USPC ..................................................... 422/554, 88
See application file for complete search history.

(56) References Cited

U.S. PATENT DOCUMENTS

| | | | | |
|---|---|---|---|---|
| 5,225,165 A | * | 7/1993 | Perlman | 422/548 |
| 6,475,774 B1 | * | 11/2002 | Gupta | 435/287.2 |
| 6,767,511 B1 | * | 7/2004 | Rousseau | 422/73 |

FOREIGN PATENT DOCUMENTS

| | | |
|---|---|---|
| EP | 0 325 874 A1 | 8/1989 |
| WO | WO-03/065047 A | 8/2003 |
| WO | WO-2005/084263 A | 9/2005 |

* cited by examiner

*Primary Examiner* — Sam P Siefke
*Assistant Examiner* — Bryan Kilpatrick
(74) *Attorney, Agent, or Firm* — Venable LLP; Michael A. Gollin; Steven J. Schwarz

(57) ABSTRACT

A reaction well, intended for use in an automatic analysis appliance and including an opening at its top end and one or two flaps for partially closing said opening, the flaps being separated by a slot enabling a liquid injection or sampling needle to pass through, and preventing stirrer means contained within the well from escaping.

17 Claims, 1 Drawing Sheet

REACTION WELL FOR AN AUTOMATIC ANALYSIS APPLIANCE

FIELD OF THE INVENTION

The invention relates to a reaction well, designed to be used in an automatic analysis appliance for analyzing chemical or biological samples.

BACKGROUND OF THE INVENTION

Wells of this type are known from documents EP-A-0 325 874 and WO-A-03/065047, and are used for determining the time required for the physical state of a medium to change, in particular for determining the coagulation time of a blood sample, each well being open at its top end and including a circularly arcuate bottom forming a track for a ferromagnetic material ball that can be caused to move in the well in periodic motion by means of an external magnetic field, variations in amplitude and/or frequency of the motion of the ball being representative of the physical state of the blood sample.

In document WO-A-03/065047, the wells containing the balls are fastened side by side in a detachable manner on a flexible support film that closes their top ends and that can be wound on a reel in order to feed an automatic analysis appliance and cause the wells to move in succession through the appliance.

That film includes a series of slots or orifices situated in register with the well openings for depositing samples and reagents into the wells.

In order to fasten the wells onto the film, each well includes, at its top end, two lateral tabs formed with protruding studs designed to be engaged by force in lateral perforations of the film, the tabs of the wells fastened to the film forming a rack enabling the film and well assembly to be driven by meshing with a cog belt or the like.

Those known means present numerous advantages but also a few drawbacks:
  the wells must be fastened to the film, and then removed from said film after use, which operations are not always carried out in a perfect manner, with risk of premature or late removal of the wells. Those operations also represent a cost that is not negligible relative to the cost of the wells and that is in addition to the cost of the film to which the wells are fastened;
  while the wells are being moved, the balls contained therein might be poorly retained by the film and they might be ejected from the wells. In this event, the planned analyses cannot be performed correctly in the wells and must be re-done in wells containing balls, and that results in a loss of samples, of reagents, and of time.

OBJECT AND SUMMARY OF THE INVENTION

A particular object of the present invention is to avoid those drawbacks of the prior art.

For this purpose the invention proposes a reaction well, designed for use in an automatic analysis appliance and containing stirrer means for stirring a fluid medium, the well including an opening at its top end and having at least one flap for partially closing said opening, the flap extending substantially in the plane of the opening, from one side thereof towards the opposite side.

In a variant, the well includes two flaps for partially closing the above-mentioned opening, said flaps extending substantially towards each other in the plane of the opening from two opposite sides of the opening.

In the closed position, the flap(s) prevent(s) the stirrer means contained within the well from escaping from said well, while allowing a needle to pass for sampling or injecting liquid in the well.

Advantageously, the flap(s) is/are formed by being integrally molded with the well.

In a first embodiment of the invention, the flap(s) is/are molded onto the top end of the well directly in their closed position.

In this embodiment, the stirrer means, such as a ball of ferromagnetic material, are placed in the well before molding on the above-mentioned flap(s).

In another embodiment of the invention, the or each flap is injection-molded with the well, in an initial position disengaging the opening of the well, then said flap is folded down into a position for partially closing the opening by being pivoted about its connection zone with a side of the opening.

In this embodiment, the stirrer means, such as a ball of ferromagnetic material, are placed in the well after molding the above-mentioned tab(s) and before folding it/them down into the closed position.

The plastics material from which the well is made presents rigidity that allows the or each flap to be folded down from its initial position into its partially-closed position in which it partially closes the well opening, and that causes the flap connection zone to break at a later time when the flap pivots from its partially-closed position into its initial position.

This characteristic effectively prevents the wells, which are consumables that are disposable after use, from being re-used a second time, or a plurality of times after a first use, with all the risks of contamination that that involves.

Advantageously, the well of the invention includes holding means for holding the or each above-mentioned flap in its closed position, these holding means comprising for example at least one protruding stud formed on an side of the opening, said stud extending substantially in the plane of the opening.

In a variant embodiment, the stirrer means contained within the well are not constituted by a ball of ferromagnetic material, but by a lever pivotally mounted on the top portion of the well.

BRIEF DESCRIPTION OF THE DRAWINGS

The invention can be understood better and other characteristics, details, and advantages of the invention appear more clearly on reading the following description given by way of example and with reference to the accompanying drawing, in which.

MORE DETAILED DESCRIPTION

Figure 1:
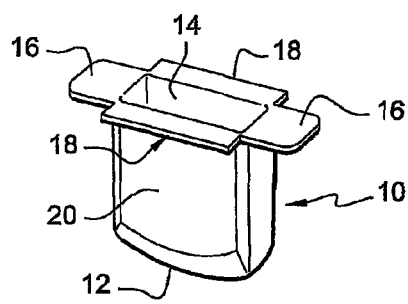
FIG. 1 is a diagrammatic perspective view of a well of the invention, coming out of a production mold.
Figure 2:
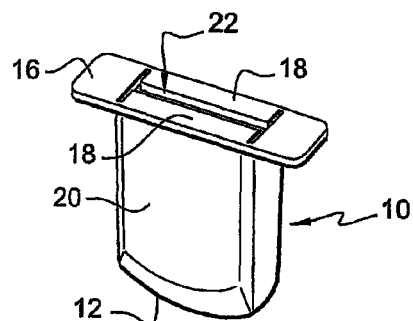
FIG. 2 is a diagrammatic perspective view of the well in a position of use.
Figure 3:
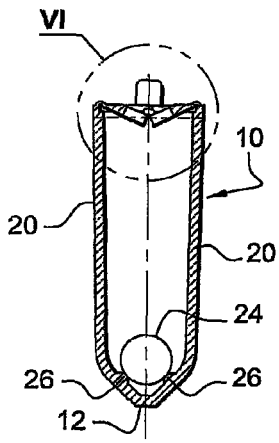
FIG. 3 is a diagrammatic cross-section view of a well in a particular embodiment of the invention.
Figure 4:
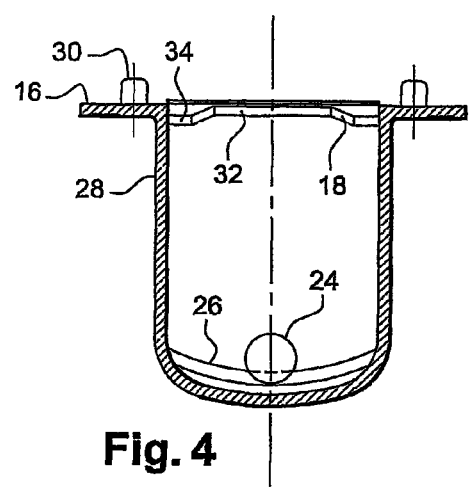
FIG. 4 is a diagrammatic longitudinal section view of the well shown in FIG. 3.

Reference is made initially to FIGS. 1 and 2, which are diagrams showing a well 10 of the invention, said well being generally in the form of a parallelepiped of rectangular section with a circularly arcuate bottom 12 and an open top end 14 of rectangular shape.

The top end of the well 10 includes two tabs 16 projecting outwards from the short sides of the rectangular opening 14 and forming lugs for gripping and handling the well.

According to the invention, the top end of the well 10 also includes at least one, and preferably two, fold-down flaps 18 for partially closing the opening 14, the flaps extending outwards in the position of manufacture of the well and projecting from the two long sides of the rectangular opening 14, the two flaps having the same shape and the same dimensions, but in a variant they could also have different shapes and/or dimensions.

The zone where each flap 18 is connected to the top end of a large wall 20 of the well is designed to enable the flap 18 to be folded down into the plane of the opening 14, as shown in FIG. 2, with this folding down taking place after placing liquid stirrer means in the well, such as a ball of ferromagnetic material, a pivoting lever, or other means.

When both flaps 18 have been folded down into the plane of the top opening 14 of the well, the opening is not completely closed, the flaps 18 being separated by a slot 22, with a width of about 2 mm for example, thereby enabling a liquid injection or sampling needle to pass through, and preventing the stirrer means contained within the well from escaping.

The material from which the well is made and the characteristics of the zones connecting the flaps 18 to the large faces 20 of the well are designed to prevent the flaps 18 from folding back in the opposite direction when said flaps are in their closed position shown by FIG. 2.

Thus, if it is attempted to fold the flaps 18 back outwards from their position shown in FIG. 2, this causes their links to the well to break and prevents any future use of the well.

To this end, in this embodiment, the well is made by injection-molding polyester, preferably a "crystal" polyester that is completely transparent, said substance being of rigidity that is well adapted to the folding characteristics desired for the flaps 18.

FIGS. 3 to 6 show a particular example of an embodiment of the well 10 of the invention, said well being shown in the closed position and containing stirrer means constituted by a ball 24 of ferromagnetic material.

This ball is guided on a circularly arcuate, concave track that is formed by two internal ribs 26 on the large walls 20 of the well, these circularly arcuate ribs rising a little from the middles of the large walls 20 on going towards the small walls 28 of the well.

The lugs 16 of the top end of the well 10 are of a shape that is substantially trapezoidal and they include respective protruding studs 30 on their top faces, of the type that is used, in the above-mentioned prior art, to fasten wells to a film of flexible material.

The flaps 18 for closing the top end of the well include, in their longitudinal free sides remote from their zones connecting them to the well, respective notches 32 of trapezoidal shape, the two notches defining between them the above-mentioned slot 22 for introducing a sampling or injection needle into the well.

Each notch 32 is formed substantially in the middle of the free side of the corresponding flap 18 and it does not extend over the entire length of the flap.

Figure 5:
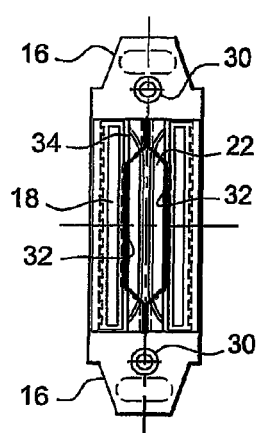
FIG. 5 is a diagrammatic plan view of the well shown in FIG. 3.

Thus, in their closed position, the two flaps 18 can be substantially in contact with each other at their longitudinal ends 34, as can be seen in the plan view of FIG. 5.

Figure 6:
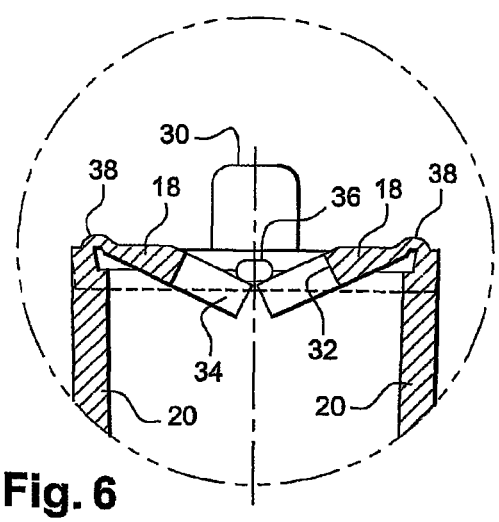
FIG. 6 is a larger-scale view of the circled detail VI of the well shown in FIG. 3.

In order to hold the flaps 18 into their closed position, two small studs 36 can be formed protruding from the short sides of the top end of the well 10, as can be better seen in FIG. 6, these small studs 36 being situated along the trajectories of the longitudinal ends 34 of the flaps 18 at the end of their folding-down strokes into the closed position and forming hard points that can be passed by pressing harder on the flaps 18 and that then prevent the flaps from returning into an open position of the well.

The zones 38 connecting the flaps 18 to the top sides of the long walls 20 of the well have a determined shape, and a thickness that is less than that of the flaps and the walls 20 so as to constitute simultaneously flexible hinges enabling the flaps 18 to be folded down into the closed position, and zones of weakness that are intended to break when it is attempted to return the flaps 18 into an open position of the well.

The flaps 18 are advantageously formed integrally with the well, by molding.

The flaps can be molded in the position shown in FIG. 1, and are thus folded down into the closed position by pivoting through approximately 180° about their zones connected to the well.

In a variant, they can be molded to extend the large walls 20 of the well and are thus folded down into a closed position by pivoting through approximately 90°.

The flaps can also be made directly in their closed position at the top end of the well, by being molded onto the top sides of the long walls 20 of the well.

Whatever the method of manufacture, the flaps 18 can be constituted from the same material as the well or from a material that is different, but that is compatible with the material of the well.

Whereas the well is made of a transparent material, the flaps may possibly be made of an opaque material if it is useful to protect the liquid medium contained in the well from ambient light.

What is claimed is:

1. A reaction well, intended for use in an automatic analysis appliance and containing a stirrer device to stir a fluid medium, the well including
    an opening at its top end; and
    at least one flap integrally molded with the well, the at least one flap extending substantially in the plane of the opening and partially from one side of the opening towards an opposite side of the opening to partially close said opening and thereby define an open slot at the top end of the well.

2. A well according to claim 1, further comprising two flaps to partially close said opening, said flaps extending substantially towards each other in said plane of the opening when they are in their position for partially closing the opening.

3. A well according to claim 1, wherein the at least one flap in the closed position prevents the stirrer device contained within the well from escaping.

4. A well according to claim 2, wherein the two flaps comprise substantially similar dimensions and shape.

5. A well according to claim 1, wherein the at least one flap comprises the same medium as the well.

6. A well according to claim 1, wherein the at least one flap is molded onto the sides of the top end of the well.

7. A well according to claim 6, wherein the at least one flap is molded in its position to partially close the opening of the well.

8. A well according to claim 1, wherein the at least one flap is injection-molded with the well, in an initial position disengaging the opening of the well, then said at least one flap is folded down into a position for partially closing the opening by being pivoted about its connection zone with a side of the opening.

9. A well according to claim 8, wherein the well comprises a plastics material presenting rigidity that allows the at least one flap to be folded down from an initial position into a partially-closed position in which it partially closes the well opening, and that causes the flap connection zone to break at a later time when the at least one flap pivots from its partially-closed position into its initial position.

10. A well according to claim 8, further comprising a holding device to hold the at least one flap in the partially-closed position.

11. A well according to claim 10, wherein the holding device comprises at least one protruding stud on one edge of the opening, said stud extending in the plane of the opening.

12. A well according to claim 1, wherein the at least one flap in the closed position defines the open slot to allow a needle to be introduced through the slot to inject or sample liquid in the well.

13. A well according to claim 2, wherein the two flaps are separated from each other by a distance of about 2 mm in the partially-closed position to define the open slot.

14. A well according to claim 1, further comprising two lateral lugs at the top end of the well.

15. A well according to claim 14, wherein the two lugs project outwards from two short sides of the opening of the well, the at least one flap being attached to one of two long sides of the opening.

16. A well according to claim 1, wherein the at least one flap is opaque.

17. A well according to claim 1, wherein the at least one flap includes a trapezoidal notch formed in a free side of said at least one flap.

* * * * *